(12) United States Patent
Sabottke et al.

(10) Patent No.: US 8,083,946 B2
(45) Date of Patent: *Dec. 27, 2011

(54) CHEMICALLY CROSS-LINKED POLYMERIC MEMBRANES AND METHOD OF USE

(75) Inventors: Craig Y. Sabottke, Annandale, NJ (US); Bal K. Kaul, Fairfax, VA (US); Dennis G. Peiffer, Annandale, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 540 days.

This patent is subject to a terminal disclaimer.

(21) Appl. No.: 11/890,225

(22) Filed: Aug. 3, 2007

(65) Prior Publication Data

US 2008/0035572 A1 Feb. 14, 2008

Related U.S. Application Data (60) Provisional application No. 60/836,423, filed on Aug. 8, 2006.

(51) Int. Cl.
*B01D 71/06* (2006.01)
*B01D 71/64* (2006.01)
*B01D 71/48* (2006.01)
*B01D 61/00* (2006.01)

(52) U.S. Cl. ........ 210/650; 210/652; 210/653; 210/654; 210/500.39; 210/500.37; 427/245; 96/4; 96/6

(58) Field of Classification Search .................. None
See application file for complete search history.

(56) References Cited

U.S. PATENT DOCUMENTS

| | | | |
|---|---|---|---|
| 4,650,574 A | 3/1987 | Hilgendorff et al. | |
| 4,705,540 A | 11/1987 | Hayes | |
| 4,717,393 A | 1/1988 | Hayes | |
| 4,853,128 A | 8/1989 | Wrasidio et al. | |
| 4,880,442 A | 11/1989 | Hayes | |
| 4,914,064 A | 4/1990 | Schucker | |
| 4,929,358 A | 5/1990 | Koenitzer | |
| 4,944,880 A | 7/1990 | Ho et al. | |
| 4,946,594 A | 8/1990 | Thaler et al. | |
| 4,962,270 A | 10/1990 | Feimer et al. | |
| 4,990,275 A | 2/1991 | Ho et al. | |
| 5,039,418 A | 8/1991 | Schucker | |
| 5,085,676 A | 2/1992 | Ekiner et al. | |
| 5,110,879 A | 5/1992 | Chung et al. | |
| 5,130,017 A | 7/1992 | Schucker | |
| 5,138,023 A | 8/1992 | Sartori et al. | |
| 5,262,056 A | 11/1993 | Koros et al. | |
| 5,275,726 A | 1/1994 | Feimer et al. | |
| 5,445,731 A | 8/1995 | Tuohey et al. | |
| 5,550,199 A | 8/1996 | Ho et al. | |
| 5,591,250 A | 1/1997 | Stern et al. | |
| 5,670,051 A | 9/1997 | Pinnau et al. | |
| 5,670,052 A | 9/1997 | Ho et al. | |
| 5,685,990 A | 11/1997 | Saugmann et al. | |
| 5,756,643 A * | 5/1998 | Ho et al. | 528/272 |
| 5,855,647 A | 1/1999 | Li et al. | |
| 6,096,114 A | 8/2000 | Li et al. | |
| 6,203,713 B1 | 3/2001 | Tanny | |
| 6,383,258 B1 | 5/2002 | Simmons | |
| 6,645,383 B1 | 11/2003 | Lee et al. | |
| 6,660,062 B2 | 12/2003 | Liu et al. | |
| 7,247,191 B2 | 7/2007 | Koros et al. | |
| 7,265,182 B2 | 9/2007 | Lin et al. | |
| 7,422,623 B2 | 9/2008 | Ekiner et al. | |
| 2004/0000513 A1 | 1/2004 | Colling et al. | |
| 2004/0004040 A1 | 1/2004 | Colling et al. | |
| 2005/0003204 A1 | 1/2005 | Frankel et al. | |
| 2006/0081500 A1 | 4/2006 | Bitterlich et al. | |

FOREIGN PATENT DOCUMENTS

| | | |
|---|---|---|
| WO | WO 2006/040307 A1 | 4/2006 |
| WO | WO 2006/066269 A2 | 6/2006 |

* cited by examiner

*Primary Examiner* — Krishnan S Menon
(74) *Attorney, Agent, or Firm* — Bruce M. Bordelon (57) ABSTRACT

This invention relates to the fabrication of a polymeric membrane and a process for utilizing the polymeric membrane for separating components of a feedstream. More particularly, but not by way of limitation, this invention relates to the fabrication of a polymeric membrane and a process for utilizing the polymeric membrane in the separation of aromatics from a hydrocarbon based feedstream. The membranes of the present invention possess low soft segment glass transition temperatures and improved separation characteristics.

14 Claims, 9 Drawing Sheets

CHEMICALLY CROSS-LINKED POLYMERIC MEMBRANES AND METHOD OF USE

CROSS REFERENCE TO RELATED APPLICATION

Non-Provisional Application based on Provisional Application No. 60/836,423 filed Aug. 8, 2006

CROSS-REFERENCE TO RELATED APPLICATIONS

This application is a United States utility application which claims priority to U.S. Provisional Patent Application Ser. No. 60/836,423, filed Aug. 8, 2006.

FIELD OF THE INVENTION

This invention relates to the composition of a polymeric membrane, an apparatus utilizing said polymeric membrane, and a process for utilizing said polymeric membrane for separating components of a feedstream. More particularly, but not by way of limitation, this invention relates to the composition of a polymeric membrane an apparatus utilizing said polymeric membrane, and a process for utilizing a polymeric membrane in the separation of aromatics from a hydrocarbon based feedstream.

BACKGROUND OF THE INVENTION

Polymeric membrane based separation processes such as reverse osmosis, pervaporation and perstraction are conventional. In the pervaporation process, a desired feed component, e.g., an aromatic component, of a mixed liquid feed is preferentially absorbed by the membrane. The membrane is exposed at one side to a stream comprised of a mixture of liquid feeds and a vacuum is applied to the membrane at the opposite side so that the adsorbed component migrates through the membrane and is removed as a vapor from the opposite side of the membrane via a solution-diffusion mechanism. A concentration gradient driving force is therefore established to selectively pass the desired components through the membrane from its upstream side to its downstream side.

The perstraction process is utilized to separate a liquid stream into separate products. In this process, the driving mechanism for the separation of the stream into separate products is provided by a pressure or a concentration gradient exerted across the membrane. Certain components of the fluid will preferentially migrate across the membrane because of the physical and compositional properties of both the membrane and the process fluid, and will be collected on the other side of the membrane as a permeate. Other components of the process fluid will not preferentially migrate across the membrane and will be swept away from the membrane area as a retentate stream. Due to the pressure mechanism of the perstraction separation, it is not necessary that the permeate be extracted in the vapor phase. Therefore, no vacuum is required on the downstream (permeate) side of the membrane and permeate emerges from the downstream side of the membrane in the liquid phase. Typically, permeate is carried away from the membrane via a swept liquid.

The economic basis for performing such separations is that the two products achieved through this separation process (i.e., retentate and permeate) have a refined value greater than the value of the unseparated feedstream. Membrane technology based separations can provide a cost effective and energy efficient processing alternative for performing the product separation of such feedstreams. Conventional separation processes such as distillation and solvent extraction can be costly to install and operate in comparison with membrane process alternatives. These conventional based processes can require a significant amount of engineering, hardware and construction costs to install and also may require high levels of operational and maintenance personnel costs to maintain the associated facilities in an operating status. Additionally, most of these processes require the heating of the process streams to relatively high temperatures in order to separate different components during the processing steps resulting in higher energy costs than are generally required by low-energy membrane separation processes.

In general, the membrane technology in the present art has the benefit of lower per unit energy costs per volume of separation than the conventional technologies in present art. However, a major obstacle in perfecting the commercial operation of membrane separation technologies is to improve the flux and selectivity characteristics of the membrane systems in order to make the construction costs and separation efficiencies of membrane technologies economically viable, for example, on a refinery scale operations and on-board vehicle separation processes.

A myriad of polymeric membrane compositions have been developed over the years. Such compositions include polyurea/urethane membranes (U.S. Pat. No. 4,914,064); polyurethane imide membranes (U.S. Pat. No. 4,929,358); polyester imide copolymer membranes (U.S. Pat. No. 4,946,594); polyimide aliphatic polyester copolymer membranes (U.S. Pat. No. 4,990,275); and diepoxyoctane crosslinked/esterfied polyimide/polyadipate copolymer (diepoxyoctane PEI) membranes (U.S. Pat. No. 5,550,199)). Additional membranes developed from the polycarbonate membrane family include polyphthalate carbonate membranes (U.S. Pat. No. 5,012,035), non-porous polycarbonate membranes (U.S. Pat. No. 5,109,666), and polyarylate membranes (U.S. Pat. No. 5,012,036).

Major factors affecting the performance (i.e., the selectivity and flux rate) of a polymeric membrane are the composition of the membrane material, the concentration of the membrane material in solution, the curing or chemical reaction methods, and the final thickness of the cast membrane. In general, for a given polymeric membrane composition, the flux across a given membrane is approximately inversely proportional to the thickness of the membrane. Therefore, the active portion of membranes in the prior art are generally cast as very thin films (on the order of 0.1 to 50 micron thickness) in order to derive the selectivity benefit of the membrane while maximizing the flux characteristics of the membrane. However, problems associated with the fabrication and operation of thin membranes include voids and inconsistencies in the membrane structure which affect the membrane performance as well as mechanical instability of the membrane due to their thin structural profile.

Copolymeric membranes of the prior art may be comprised of "soft segments" and "hard segments" and may undergo a "thermal cross-linking" at relatively high temperatures (above approximately 300° C./572° F.) to provide an interchain structural framework to impart mechanical and thermal strength to the membrane. While the soft segments of the polymer provide the active area for the selective diffusion of the permeate through the membrane, they generally possess limited structural and thermal strength characteristics. Therefore, in order to provide the membrane sufficient structural integrity, the polymer soft segments are polymerized with the hard polymer segments to form copolymer chains. In this way, the hard segments of the copolymer chain provide the necessary mechanical and thermal strength to the overall membrane. However, these hard segments of the copolymer chains possess limited, if any, permeability of the process stream components. The problem that exists is that the copolymer membranes that result from thermal cross-linking, while relatively mechanically stable, have limited flux and/or selectivity characteristics.

Therefore, there exists in the industry a need for selective membrane compositions with improved membrane performance characteristics.

SUMMARY OF THE INVENTION

The present invention includes a polymeric membrane composition. Additionally, the present invention includes the use of this membrane composition in a membrane assembly and separations processes.

A preferred embodiment of the present invention is a polymeric membrane composition, comprising a dianhydride, a diamine, a cross-linking agent and a difunctional dihydroxy polymer selected from:

a) dihydroxy end-functionalized ethylene propylene copolymers with an ethylene content from about 25 wt % to about 80 wt %;

b) dihydroxy end-functionalized ethylene propylene diene terpolymers with an ethylene content from about 25 wt % to about 80 wt %;

c) dihydroxy end-functionalized polyisoprenes; dihydroxy end-functionalized polybutadienes; dihydroxy end-functionalized polyisobutylenes;

d) dihydroxy end-functionalized acrylate homopolymers, copolymers and terpolymers; dihydroxy end-functionalized methacrylate homopolymers, copolymers and terpolymers; and mixtures thereof, wherein the mixtures of acrylate and methacrylate monomers range from $C_1$ to $C_{18}$;

e) dihydroxy end-functionalized condensation homopolymers, copolymers, terpolymers and higher order compositions of structurally different monomers, including alcohol-terminated end-functionalized esters and dihydroxy end-functionalized multimonomer polyesters; and mixtures thereof;

wherein the polyalkyladipate structures range from $C_1$ to $C_{18}$;

f) dihydroxy end-functionalized perfluoroelastomers;

g) dihydroxy end-functionalized urethane homopolymers, copolymers, terpolymers, and higher order compositions of structurally different monomers;

h) dihydroxy end-functionalized carbonate homopolymers, copolymers, terpolymers, and higher order compositions of structurally different monomers;

i) dihydroxy end-functionalized ethylene alpha-olefin copolymers; dihydroxy end-functionalized propylene alpha-olefin copolymers; dihydroxy end-functionalized ethylene propylene alpha-olefin terpolymers;

wherein the alpha-olefins are linear or branched and range from $C_3$ to $C_{18}$;

j) dihydroxy end-functionalized styrene homopolymers, copolymers, terpolymers, and higher order compositions of structurally different monomers;

k) dihydroxy end-functionalized silicone homopolymers, copolymers, terpolymers, and higher order compositions of structurally different monomers;

l) dihydroxy end-functionalized styrene butadiene copolymers; dihydroxy end-functionalized styrene isoprene copolymers; and m) dihydroxy end-functionalized styrene butadiene block copolymers; and dihydroxy end-functionalized styrene isoprene block copolymers;

wherein the polymeric membrane is comprised of a hard segment and soft segment, and Absorbance Infra-red Spectrum of the membrane has an Aliphatic C—H Area to Aromatic C—H Area ratio of at least 10.

In another preferred embodiment, the soft segment has a glass transition temperature, $T_g$, less than 77° F. (25° C.). More preferably, the glass transition temperature, $T_g$, of the soft segment is less than 32° F. (0° C.), and even more preferably, the glass transition temperature, $T_g$, of the soft segment is less than –13° F. (–25° C.).

In another preferred embodiment, the polymeric membrane is utilized in a polymeric membrane assembly in combination with a support material selected from polytetrafluoroethylene, aromatic polyamide fibers, porous metals, sintered metals, porous ceramics, polyester, nylon, activated carbon fibers, latex, silicone, polyvinylfluoride, polyvinylidenefluoride, polyurethanes, polypropylenes, polyethylenes, polycarbonates, polysulfones, polyphenylene oxides, metal foams, polymer foams, silica, porous glass, mesh screens, and combinations thereof.

In yet another preferred embodiment, the polymeric membrane assembly is incorporated into a support configuration selected from flat plate elements, wafer elements, spiral-wound elements, porous monoliths, porous tubes, and hollow fiber elements.

In still another preferred embodiment, a polymeric membrane assembly of the present invention is utilized in a separation process for separating an aromatic rich permeate stream from a hydrocarbon feedstream. In another embodiment, a permeate stream rich in sulfur heteroatoms is separated from a hydrocarbon feedstream. In still another embodiment, a permeate stream rich in nitrogen heteroatoms is separated from a hydrocarbon feedstream.

DETAILED DESCRIPTION OF THE PREFERRED EMBODIMENTS

The present invention solves the problem in the prior art by relying on a combination of specific polymer compositions and low-energy chemical reactions for the cross-linking of the membrane polymer chains in order to produce a final membrane composition with improved selectivity and flux characteristics. This invention allows for chemical bonding of the polymer chains at low heat input wherein it is desirable that the heat energy utilized in fabrication is closely limited to the amount necessary to support the endothermic chemical cross-linking reactions. As a result, it is believed that the resulting membranes have limited polymer soft segment degradation and improved polymer chain structure and membrane morphology wherein the polymer chain-to-chain orientation and active polymer segment retention is superior to comparable membranes of the prior art. The improved final chain structure, low-energy, uniform polymer orientation and increased soft segment concentration in the membrane morphology of the present invention results in improved membrane flux rates and selectivities while maintaining mechanical stability of the resultant membranes.

As used herein, the term "hydrocarbon" means an organic compound having a predominantly hydrocarbon character. Accordingly, organic compounds containing one or more non-hydrocarbon radicals (e.g., sulfur or oxygen) would be within the scope of this definition. As used herein, the terms "aromatic hydrocarbon" or "aromatic" means a hydrocarbon-based organic compound containing at least one aromatic ring. The rings may be fused, bridged, or a combination of fused and bridged. In a preferred embodiment, the aromatic species separated from the hydrocarbon feed contains one or two aromatic rings. The terms "non-aromatic hydrocarbon" or "non-aromatic" or "saturate" means a hydrocarbon-based organic compound having no aromatic cores. Also as used herein, the terms "thermally cross-linked" or "thermal cross-linking" means a membrane curing process at curing temperatures typically above about 250 to 300° C. (482 to 572° F.) characterized by hydrogen bonding of neighboring polymeric chains in solution. The term "chemically cross-linked" or "chemical cross-linking" means a chemical curing process characterized by the principal reaction of chemical bonding of neighboring polymeric chains in solution via imidization thereby forming a three-dimensional polymer network. Also as used herein, the term "selectivity" or "aromatic selectivity" means the ratio of the desired component(s) in the permeate to the non-desired component(s) in the permeate divided by the ratio of the desired component(s) in the feedstream to the non-desired component(s) in the feedstream. Also, the term "flux" or "normalized flux" is defined the mass rate of flow of the permeate across a membrane, normally expressed in units of $Kg/m^2$-day, $Kg/m^2$-hr, $Kg$-$\mu m/m^2$-day, or $Kg$-$\mu m/m^2$-hr.

In a preferred embodiment, embodiment, the present invention includes the composition and use of a polyimide polymer membrane comprising soft and hard polymer segments wherein the glass transition temperature, ($T_g$), of the soft segment is less than 25° C. The term glass transition temperature, ($T_g$), is well known in the art and is defined in *Thermal Characterization of Polymeric Materials* (E. A. Turi ed., Academic Press, NY, 1981). It should be noted that the glass transition temperature measurements as defined herein are measured on a final composition, cured, and "unswollen" polymer membrane (i.e., no post-cure solvents).

The synthesis of this new membrane relies on utilizing a chemical crosslinking agent in the polymer solution and chemically bonding the pendant polymer endcapping chains at effective temperatures sufficient to promote the chemical cross-linking reaction of the membrane copolymers yet low enough to retard significant loss of the polymer chain soft segments. The polymer solution can then be cast or otherwise incorporated onto a suitable membrane support utilizing various techniques known in the art. In a preferred embodiment, the polymer solution is cured at temperatures from about 212° F. to about 482° F. (100° C. to about 250° C.), preferably from about 212° F. to about 392° F. (100° C. to about 200° C.) which allows the endothermic chemical cross-linking reactions to take place during the curing and formation of the final membrane without significant loss of the critical membrane soft segment volume.

In a preferred embodiment, the present invention results in an improved polymeric membrane composition, comprising a dianhydride, a diamine, a cross-linking agent and a difunctional dihydroxy polymer selected from:

a) dihydroxy end-functionalized ethylene propylene copolymers with an ethylene content from about 25 wt % to about 80 wt %;

b) dihydroxy end-functionalized ethylene propylene diene terpolymers with an ethylene content from about 25 wt % to about 80 wt %;

c) dihydroxy end-functionalized polyisoprenes; dihydroxy end-functionalized polybutadienes; dihydroxy end-functionalized polyisobutylenes;

d) dihydroxy end-functionalized acrylate homopolymers, copolymers and terpolymers; dihydroxy end-functionalized methacrylate homopolymers, copolymers and terpolymers; and mixtures thereof, wherein the mixtures of acrylate and methacrylate monomers range from $C_1$ to $C_{18}$;

e) dihydroxy end-functionalized condensation homopolymers, copolymers, terpolymers and higher order compositions of structurally different monomers, including alcohol-terminated end-functionalized esters and dihydroxy end-functionalized multimonomer polyesters; and mixtures thereof;

wherein the polyalkyladipate structures range from $C_1$ to $C_{18}$;

f) dihydroxy end-functionalized perfluoroelastomers;

g) dihydroxy end-functionalized urethane homopolymers, copolymers, terpolymers, and higher order compositions of structurally different monomers;

h) dihydroxy end-functionalized carbonate homopolymers, copolymers, terpolymers, and higher order compositions of structurally different monomers;

i) dihydroxy end-functionalized ethylene alpha-olefin copolymers; dihydroxy end-functionalized propylene alpha-olefin copolymers; dihydroxy end-functionalized ethylene propylene alpha-olefin terpolymers;

wherein the alpha-olefins are linear or branched and range from $C_3$ to $C_{18}$;

j) dihydroxy end-functionalized styrene homopolymers, copolymers, terpolymers, and higher order compositions of structurally different monomers;

k) dihydroxy end-functionalized silicone homopolymers, copolymers, terpolymers, and higher order compositions of structurally different monomers;

l) dihydroxy end-functionalized styrene butadiene copolymers; dihydroxy end-functionalized styrene isoprene copolymers; and m) dihydroxy end-functionalized styrene butadiene block copolymers; and dihydroxy end-functionalized styrene isoprene block copolymers;

wherein the polymeric membrane is comprised of a hard segment and soft segment, and the Absorbance Infra-red Spectrum of the membrane has an Aliphatic C—H Area to Aromatic C—H Area ratio of at least 10.

It should be noted that the polymeric membrane of the present invention need not be limited to single compositions of the polymers listed above. Solutions of differing polymer compositions may be mixed and/or solutions of differing polymer molecular weights may be mixed in ratios and practices known to one of ordinary skill in the art in order to arrive at the membrane compositions and properties as disclosed herein.

In a more preferred embodiment, the present invention results in an improved polymeric membrane composition, comprising a dianhydride, a diamine, a cross-linking agent and a difunctional dihydroxy polymer selected from:

a) dihydroxy end-functionalized condensation homopolymers, copolymers, terpolymers and higher order compositions of structurally different monomers, including alcohol-terminated end-functionalized esters and dihydroxy end-functionalized multimonomer polyesters; and mixtures thereof;
wherein the polyalkyladipate structures range from $C_1$ to $C_{18}$;

b) dihydroxy end-functionalized perfluoroelastomers;

c) dihydroxy end-functionalized urethane homopolymers, copolymers, terpolymers, and higher order compositions of structurally different monomers;

d) dihydroxy end-functionalized carbonate homopolymers, copolymers, terpolymers, and higher order compositions of structurally different monomers;

e) dihydroxy end-functionalized ethylene alpha-olefin copolymers; dihydroxy end-functionalized propylene alpha-olefin copolymers; and dihydroxy end-functionalized ethylene propylene alpha-olefin terpolymers;
wherein the alpha-olefins are linear or branched and range from $C_3$ to $C_{18}$; and f) dihydroxy end-functionalized silicone homopolymers, copolymers, terpolymers, and higher order compositions of structurally different monomers;
wherein the polymeric membrane is comprised of a hard segment and soft segment, and the Absorbance Infra-red Spectrum of the membrane has an Aliphatic C—H Area to Aromatic C—H Area ratio of at least 10

In a yet an even more preferred embodiment, the present invention results in an improved polymeric membrane composition, comprising a dianhydride, a diamine, a cross-linking agent and a difunctional dihydroxy polymer selected from:

a) dihydroxy end-functionalized condensation homopolymers, copolymers, terpolymers and higher order compositions of structurally different monomers, including alcohol-terminated end-functionalized esters and dihydroxy end-functionalized multimonomer polyesters; and mixtures thereof;
wherein the polyalkyladipate structures range from $C_1$ to $C_{18}$;

b) dihydroxy end-functionalized perfluoroelastomers;

c) dihydroxy end-functionalized carbonate homopolymers, copolymers, terpolymers, and higher order compositions of structurally different monomers; and d) dihydroxy end-functionalized ethylene alpha-olefin copolymers; dihydroxy end-functionalized propylene alpha-olefin copolymers; and dihydroxy end-functionalized ethylene propylene alpha-olefin terpolymers;
wherein the alpha-olefins are linear or branched and range from $C_3$ to $C_{18}$; and
wherein the polymeric membrane is comprised of a hard segment and soft segment, and the Absorbance Infra-red Spectrum of the membrane has an Aliphatic C—H Area to Aromatic C—H Area ratio of at least 10.

In preferred embodiments of the present invention, the soft segment of the polymeric membrane also has a glass transition temperature, $T_g$, less than 77° F. (25° C.).

Figure 1:
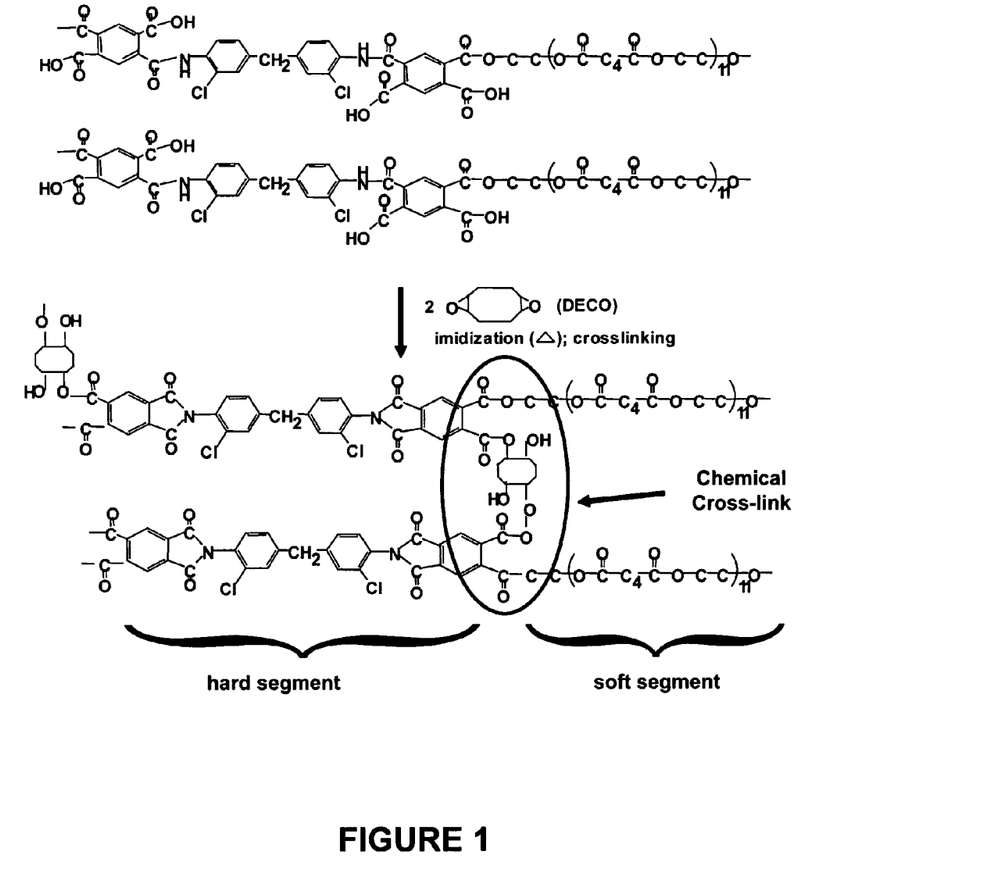
FIG. 1 illustrates the chemical cross-linking molecular synthesis of a preferred embodiment of a polymeric membrane of the present invention.

FIG. 1 illustrates the chemical cross-linking molecular synthesis of a preferred embodiment of a polymeric membrane of the present invention. As can be seen in FIG. 1, the desired reaction is promulgated by the use of a diepoxide to promote a low energy imidization reaction cross-linking the polyimide hard segments of neighboring chains resulting in a three-dimensional polymeric membrane structure. This low temperature cross-linking of the copolymer hard segments results in a membrane possessing mechanical and thermal stability while retaining a high concentration of the active soft segments which improve the flux and selectivity of the membranes of the present invention.

In a preferred embodiment, the cross-linking agent is selected from diepoxycyclooctane, diepoxyoctane, 1,3-butadiene diepoxide, glycerol diglycidyl ether, bisphenol A diglycidyl ether, 1,4-butanediol diglycidyl ether, 1,4-cyclohexanedimethanol diglycidyl ether, bisphenol F diglycidyl ether, neopentyl glycol diglycidyl ether, poly(propylene glycol) diglycidyl ether, or a mixture thereof.

The present invention results in membrane compositions wherein significant amounts of the soft polymer segments are achieved in the final, as cured composition. The high soft segment to hard segment ratios result in membranes with superior performance characteristics including improved fluxes and selectivities. The polymer membranes of the present invention include the composition and use of a polyimide polymer membrane comprising soft and hard polymer segments wherein the glass transition temperature, ($T_g$), of the soft segment is very low. The low glass transition temperatures of the present invention indicate improved soft segment retention in the final membrane composition. The term glass transition temperature, ($T_g$), is well known in the art and is defined in *Thermal Characterization of Polymeric Materials* (E. A. Turi ed., Academic Press, NY, 1981). It should be noted that the glass transition temperature measurements as defined herein are measured on a final composition, cured, and "unswollen" polymer membrane (i.e., no post-cure solvents).

In a preferred embodiment, the present invention includes polyimide polymer membranes comprising soft and hard polymer segments wherein the glass transition temperature, ($T_g$), of the soft segment is less than 77° F. (25° C.); preferably the glass transition temperature, ($T_g$), of the soft segment is less than 32° F. (0° C.). In more preferred embodiments of the present invention, polyimide polymer membranes comprising soft and hard polymer segments wherein the glass transition temperature, ($T_g$), of the soft segment is less than −13° F. (−25° C.), and even more preferably wherein the glass transition temperature, ($T_g$), of the soft segment is less than −58° F. (−50° C.) are achieved.

Figure 2:
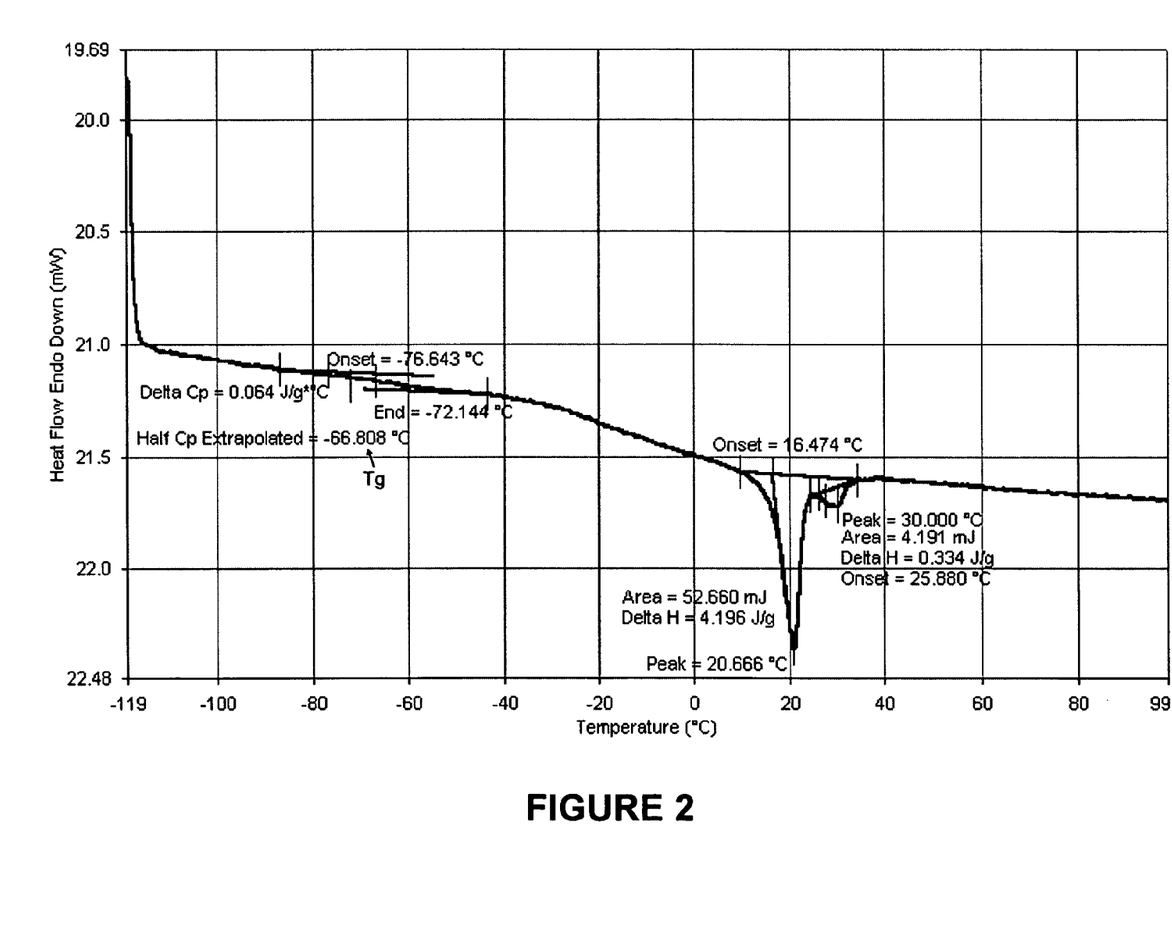
FIG. 2 is a graph of the heat flow vs. temperature testing of a membrane of the present invention exhibiting a soft segment glass transition temperature, ($T_g$), of about –66.808° C.

FIG. 2 is one illustration of the low soft segment glass transition temperature, ($T_g$), that may be obtained in a polyimide polymer membrane of the present invention. The synthesis and fabrication of the membrane possessing the $T_g$ as shown in FIG. 2 is presented in Example 3 herein. As can be seen in FIG. 2, the soft segment glass transition temperature, $T_g$, of the membrane was determined to be about −66.808° C.

The duration of time required for the curing step at elevated temperatures for fabrication of the membranes of the present invention may depend upon many factors, but generally, the membrane polymer need only be cured at these temperatures for sufficient period of time to allow the chemical crosslinking reactions to complete. This may depended on many factors such as the thickness of the incorporated membrane solution, the composition of the membrane solution, the pre- and post-preparation and incorporation techniques, the support materials, and the support configuration. Although there are not known defined limitations to the curing duration, the curing is generally performed for a duration of at least 0.5 hour. Preferably, the curing duration is about 0.5 to about 48 hours, more preferably, about 0.5 to about 24 hours, and even more preferably about 1 to about 12 hours.

In one embodiment, the copolymer solution is cooled and maintained at a temperature of less than about 100° F. (38° C.), preferably 80° F. (27° C.), more preferably less than about 40° F. (4° C.) prior to incorporation of the cross-linking agent. It is preferred if the temperature of the copolymer solution is maintained for at least 12 hours, preferably, 24 hours, and more preferably at least 72 hours prior to incorporating the cross-linking agent into the copolymer solution. This allows for the polymers in solution to equilibrate prior to forming and curing the final membrane.

In another embodiment, the copolymer solution may also undergo a purge or sweep step where gas is passed over the copolymer after the solution is integrated on the selected support, but prior to the final curing step. Preferably a gas that is non-reactive with the copolymer solution at the purging temperature is utilized in this step. Preferably the gas is comprised of nitrogen.

By controlling the heat input and allowing the chemical reaction to proceed at a controlled rate the primary reaction obtained is a chemically cross-linking imidization reaction of the neighboring polymer chains resulting in a three-dimensional polymeric chain structure in the membrane. The final curing temperature is preferably maintained as low as possible which still allows the endothermic chemical cross-linking reactions to proceed while minimizing losses of the polyadipate soft segments of the polymeric chain structures of the final membrane composition. This produces a membrane composition which has improved physical properties and separation characteristics as compared to membranes of the prior art. An example of the synthesis and composition of the membrane described in this embodiment is described in greater detail in Example 1.

While not wishing to being held to any specific theory, it is believed that the utilization of the polymer solutions of this invention in conjunction with a suitable agent for providing a chemical cross-link between adjacent polyimide hard segments in the polymer solution at low curing temperatures results in both an improved polymer chain orientation in the final membrane as well as a significantly improved retention of active soft segments in the final membrane. As a result, the membranes of the present invention possess physical and separation properties distinct from comparable membranes of the prior art. Such measurable physical differences include lower soft segment glass transition temperatures and increased soft to hard segment ratios as shown by infra-red analysis as compared to the membranes of the prior art. The membranes of the present invention also possess improved separation performance characteristics.

Figure 3:
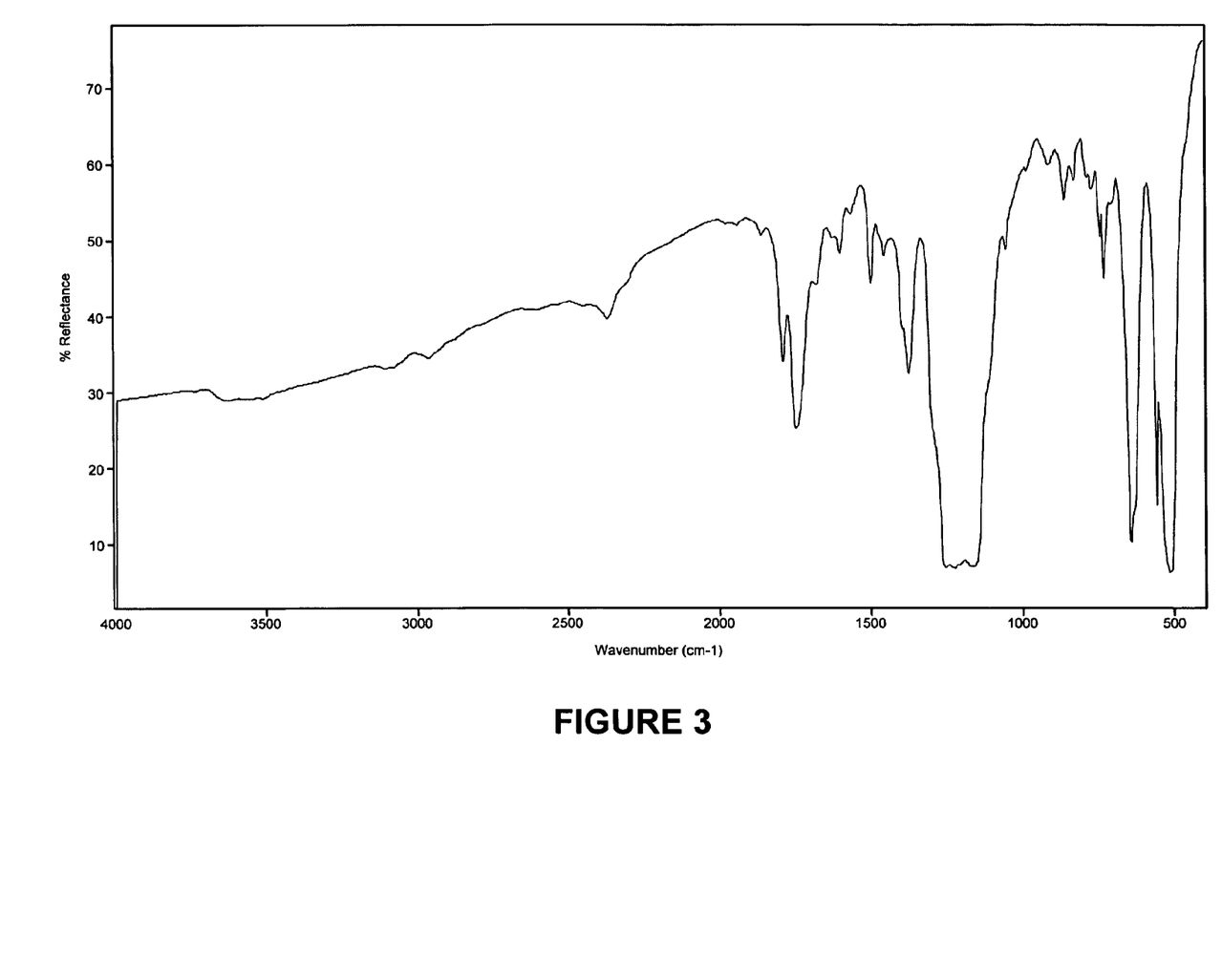
FIG. 3 is the Reflectance Spectrum of the prior art membrane in Example 3.
Figure 4:
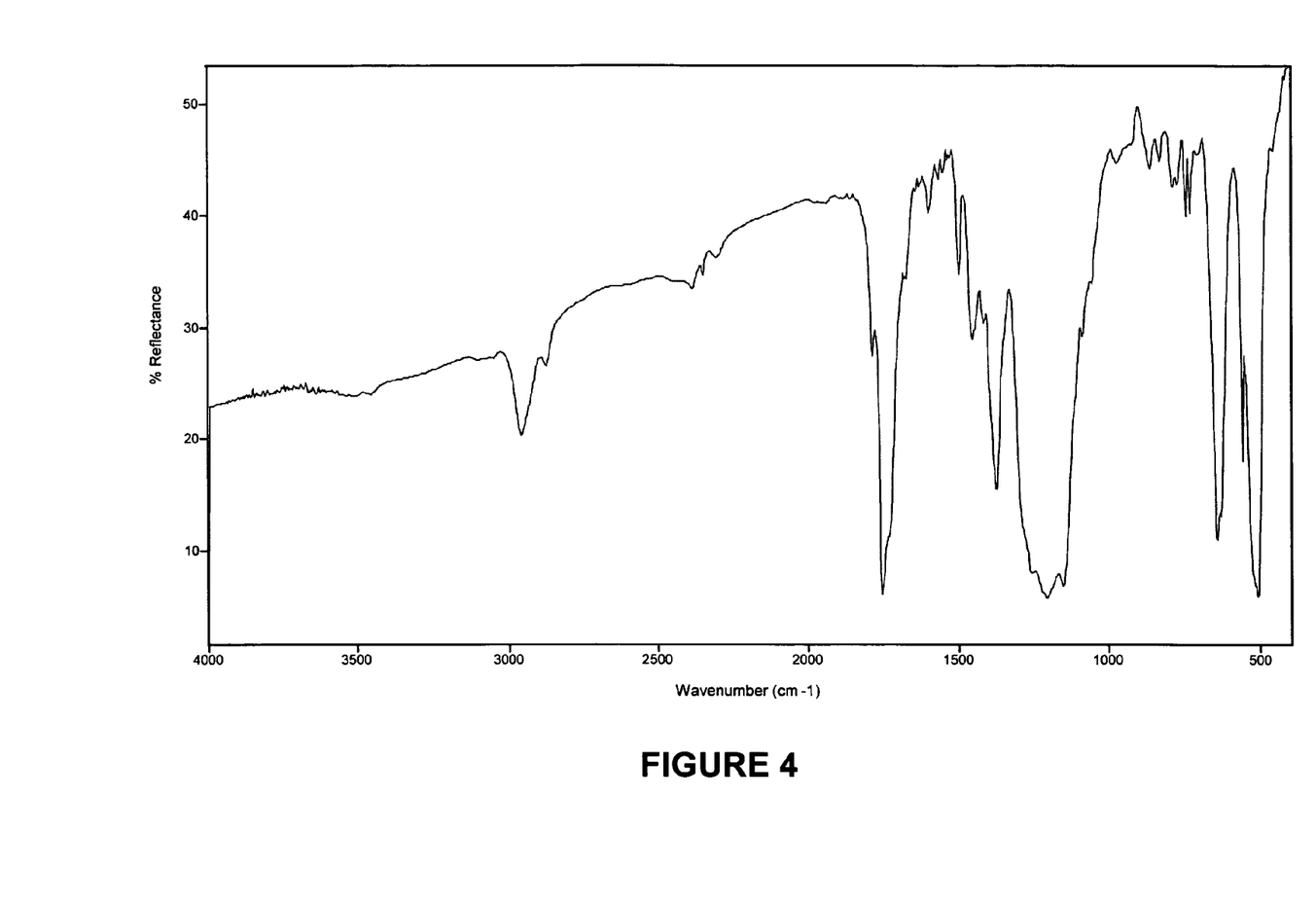
FIG. 4 is the Reflectance Spectrum of one embodiment of the present membrane in Example 3.

Example 3 illustrates the significant differences between the Diepoxycyclooctane PEI membrane of the prior art and the PEA-DECO chemically cross-linked copolymer membrane of the present invention. FIG. 3 is a graph of the results of Infra-Red ("IR") Reflectance Spectrum testing for the Diepoxycyclooctane PEI membrane of the prior art as described in U.S. Pat. Nos. 5,550,199 and 5,670,052. FIG. 4 is a graph of the results of Infra-Red ("IR") Reflectance Spectrum testing for PEA-DECO chemically cross-linked copolymer membrane of the present invention.

Figure 5:
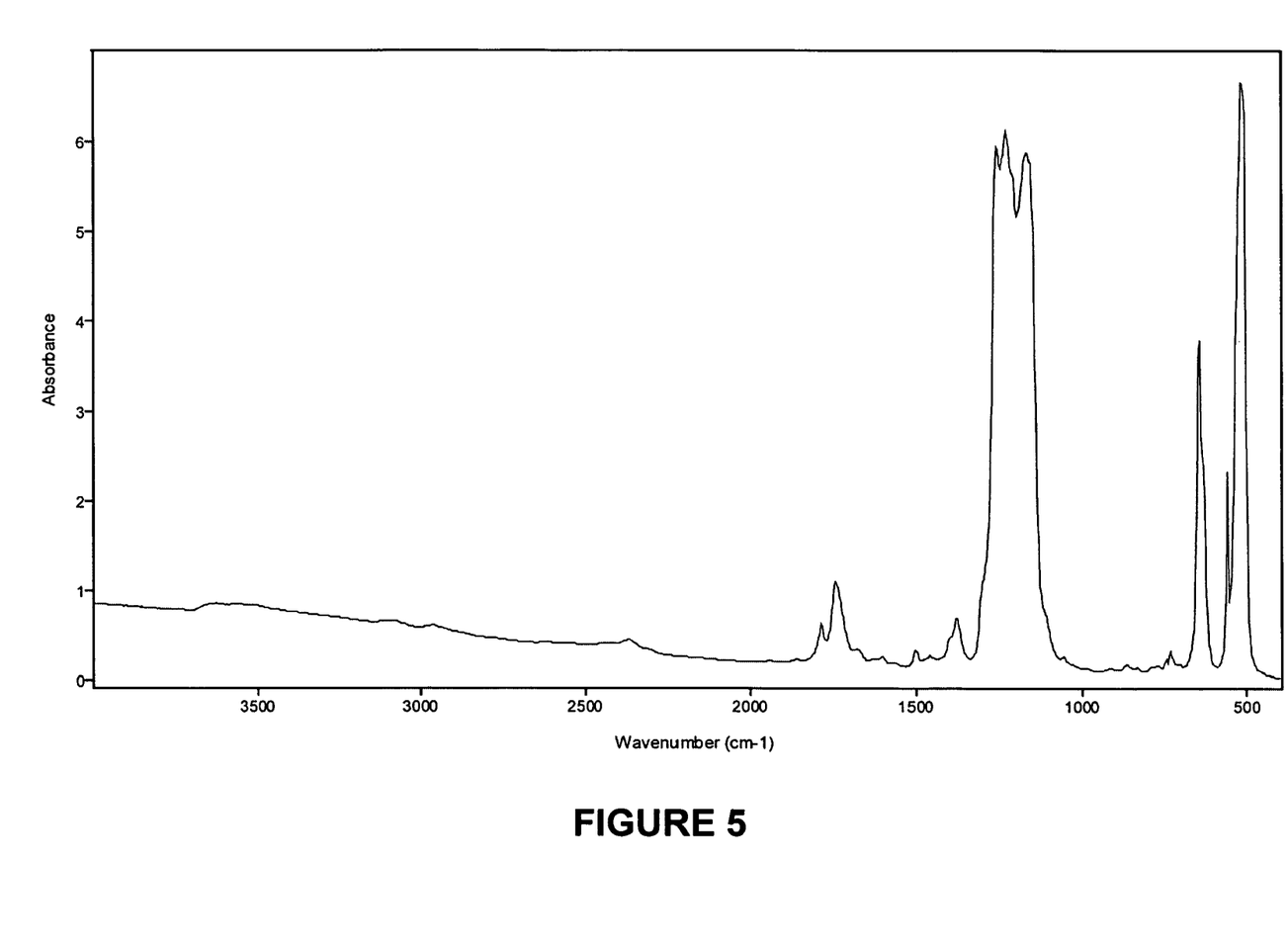
FIG. 5 is the Absorbance Spectrum of the prior art membrane in Example 3.
Figure 6:
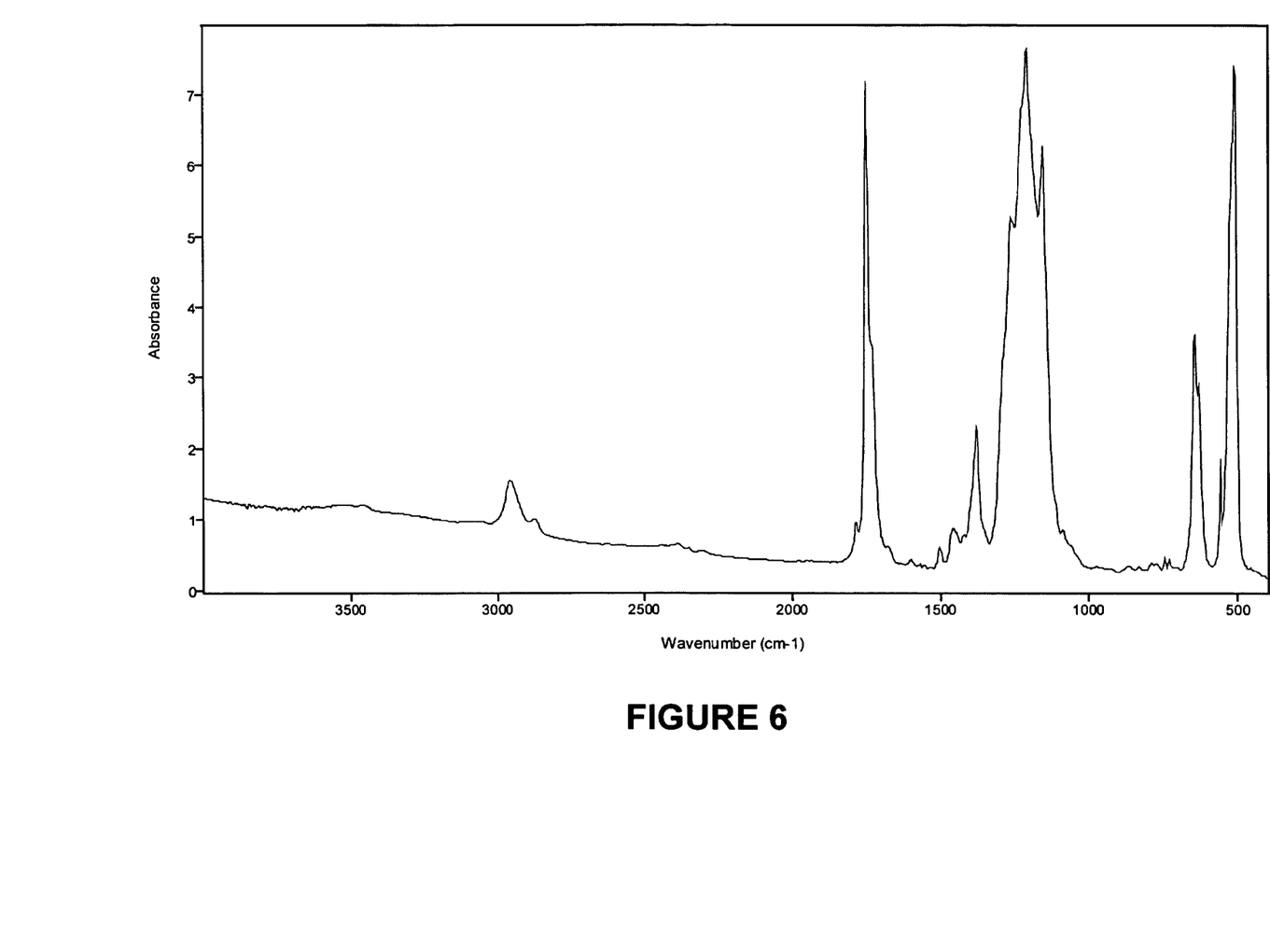
FIG. 6 is the Absorbance Spectrum of one embodiment of the present membrane in Example 3.

In order to better compare the data obtained from the IR testing, the data was converted to Absorbance values utilizing the Kubelka Monk transformation. FIG. 5 is a graph of the Absorbance Spectrum corresponding to the Reflectance Spectrum data in FIG. 3 for the Diepoxycyclooctane PEI membrane of the prior art. FIG. 6 is a graph of the Absorbance Spectrum shown corresponding to the Reflectance Spectrum data in FIG. 4 for the PEA-DECO chemically cross-linked copolymer membrane of the present invention.

As can be seen comparing FIGS. 5 and 6, significant differences can be seen in the absorbance values corresponding to the wavenumber values of about 3150 to about 2800 $cm^{-1}$, as well as the wavenumber values of 1875 to 1625 $cm^{-1}$. It should be pointed out that in the Absorbance Spectrum data, that values below about 2.0 are highly linear with respect to concentration and can be used for relative compositional comparison of molecular content within a membrane sample.

Figure 7:
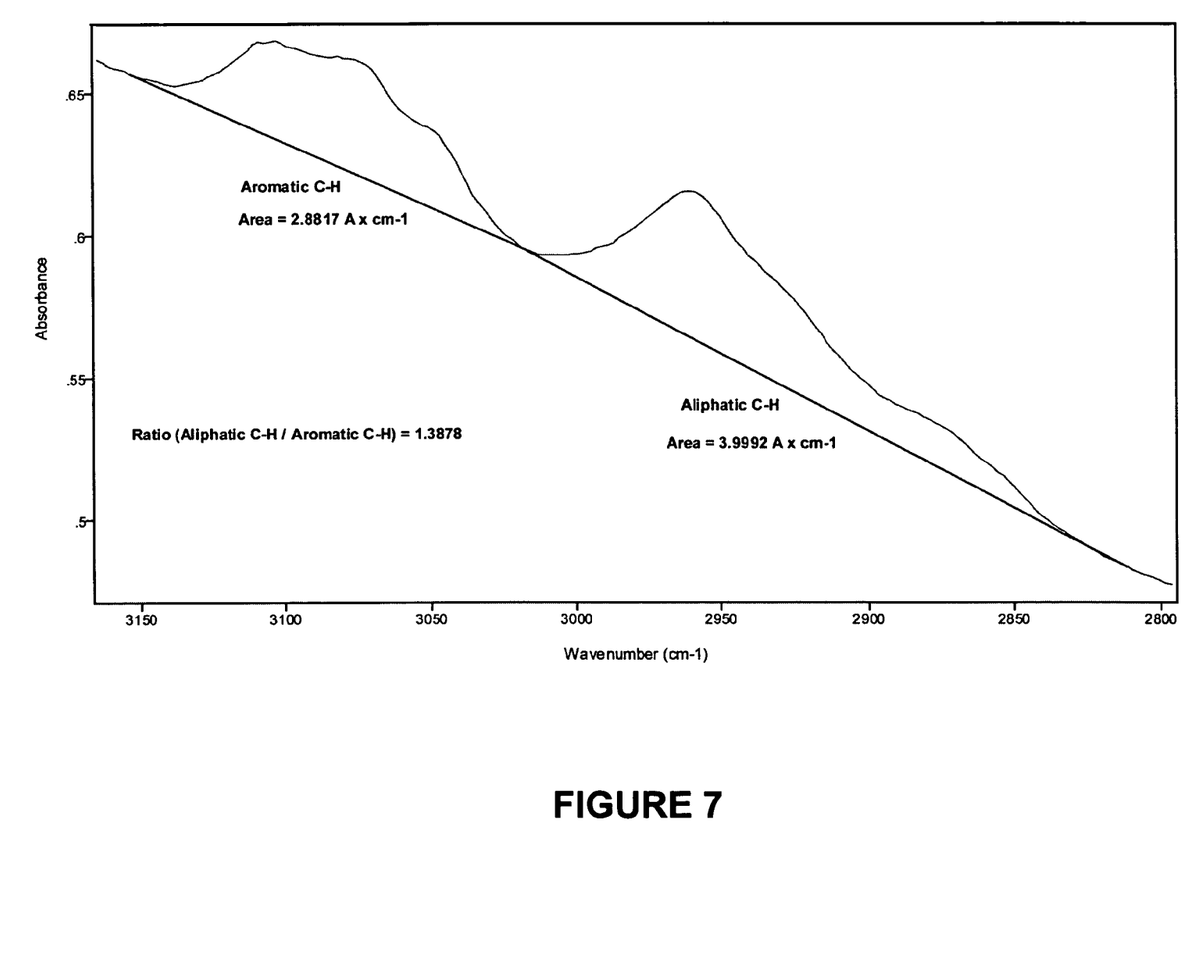
FIG. 7 is an expanded view of the Absorbance Spectrum of FIG. 5 corresponding to wavenumbers of about 3150 to 2800 $cm^{-1}$, also showing the Aromatic C—H Area and the Aliphatic C—H Area for the prior art membrane in Example 3.

FIG. 7 shows an expanded sectional view of the absorbance values corresponding to wavenumber values of about 3150 to 2800 $cm^{-1}$ from FIG. 5 for the Diepoxycyclooctane PEI membrane of the prior art. Similarly, FIG. 8 shows an expanded sectional view of the absorbance values corresponding to wavenumber values of about 3150 to 2800 $cm^{-1}$ from FIG. 6 for the PEA-DECO chemically cross-linked copolymer membrane of the present invention.

Figure 8:
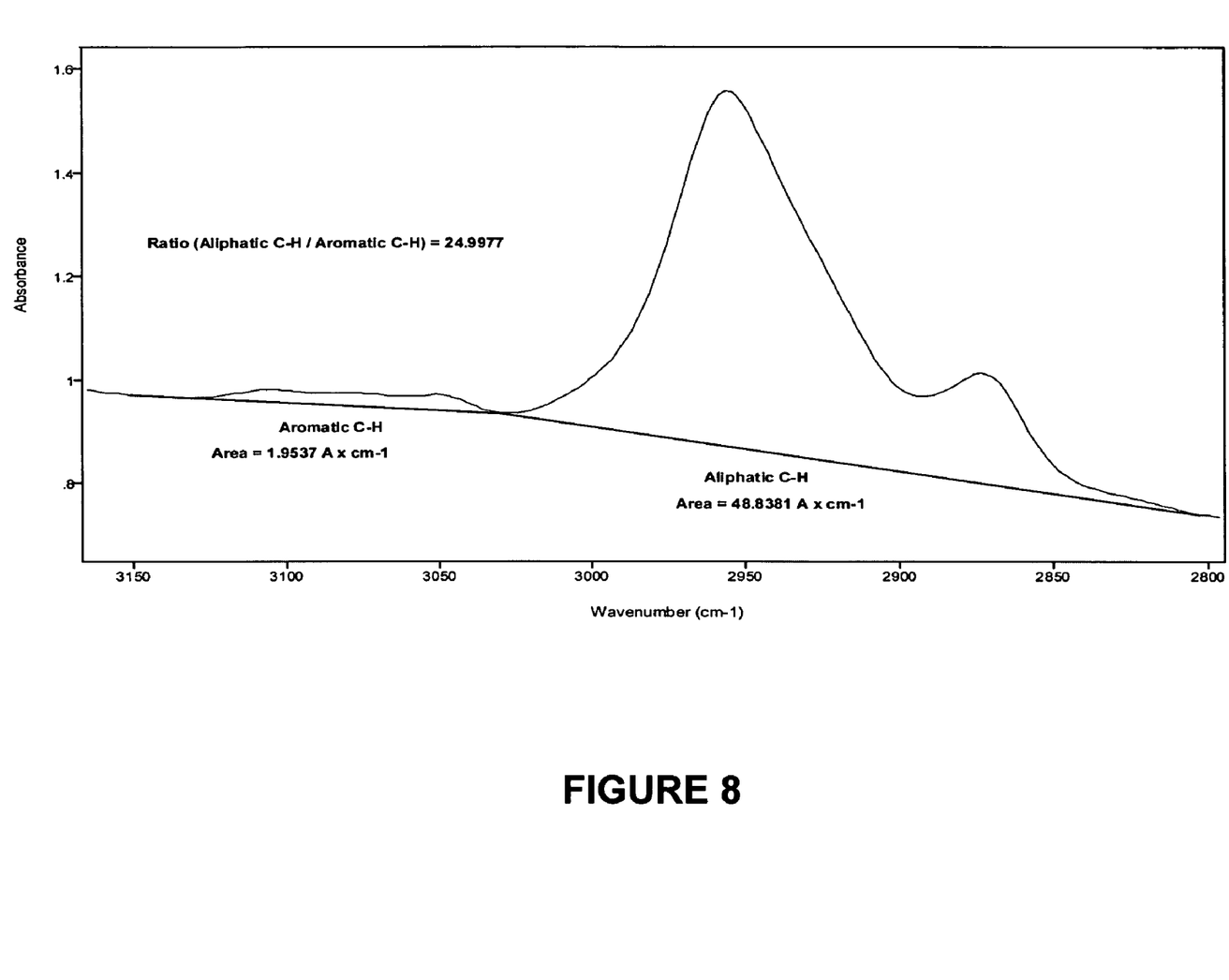
FIG. 8 is an expanded view of the Absorbance Spectrum of FIG. 6 corresponding to wavenumbers of about 3150 to 2800 $cm^{-1}$, also showing the Aromatic C—H Area and the Aliphatic C—H Area for one embodiment of the present membrane in Example 3.

In FIGS. 7 and 8, in order to evaluate the relative concentration of the aromatic C—H components associated with the membrane's hard segment and the concentration of the aliphatic C—H components associated with the membrane's soft segment, the peaked area defined by the absorbance value curve and a "baseline" must be determined for the particular component. The baseline for the aromatic C—H components is determined by a straight line drawn between the two minima on either side of the aromatic C—H component absorbance peak. In FIGS. 7 and 8, these two minima are at approximately 3150 and 3025 cm' respectively. The area defined by the integrated area between the absorbance values and the baseline between the two minima defines the Aromatic C—H Area. This Aromatic C—H Area is proportional to the hard segment content of the final polymer membrane.

In a similar manner, the baseline for the aliphatic C—H components is determined by a straight line drawn between the two minima on either side of the aliphatic C—H component absorbance peak. In FIGS. 7 and 8, these two minima are at approximately 3025 and 2800 $cm^{-1}$, respectively. The area defined by the integrated area between the absorbance values and the baseline between the two minima defines the Aliphatic C—H Area. This Aliphatic C—H Area is proportional to the soft segment content of the final polymer membrane.

Comparing these areas for the Diepoxycyclooctane PEI membrane of the prior art (FIG. 7) and the PEA-DECO chemically cross-linked copolymer membrane of the present invention (FIG. 8), it can be seen that the PEA-DECO chemically cross-linked copolymer membrane of the present invention in FIG. 8 shows a significant peak in the absorbance values corresponding to wavenumber values of about 3025 to about 2800 $cm^{-1}$ as compared with the same values in the prior art membrane shown in FIG. 7. This shows that the membrane of the present invention possess a significantly higher ratio of the aliphatic C—H soft segment as compared to the aromatic C—H hard segment.

While the absolute areas nor the absolute absorbance values between FIG. 7 and FIG. 8 should not be compared directly, the Aliphatic C—H Area/Aromatic C—H Area ratio (also referred to herein as the "Aliphatic C—H Area to Aromatic C—H Area ratio") for a given membrane is an accurate measurement of the relative concentrations of the Aromatic C—H components and the Aliphatic C—H components of the membrane. Therefore, the ratio of these areas is a suitable measurement for direct comparison of two different polymer membrane specimens. As can be seen comparing FIGS. 7 and 8, the Ratio of Aliphatic C—H Area/Aromatic C—H Area is about 1.39 for the Diepoxycyclooctane PEI membrane of the prior art. In contrast, the Ratio of Aliphatic C—H Area/Aromatic C—H Area is about 25.00 for the PEA-DECO chemically cross-linked copolymer membrane of the present invention.

In an embodiment of the present invention, the Absorbance Infra-red Spectrum of the membrane has an Aliphatic C—H Area to Aromatic C—H Area ratio of at least 10. In a preferred embodiment, the Absorbance Infra-red Spectrum of the membrane has an Aliphatic C—H Area to Aromatic C—H Area ratio of at least 15, and even more preferably an Aliphatic C—H Area to Aromatic C—H Area ratio of least 20. In a most preferred embodiment, the Absorbance Infra-red Spectrum of the membrane has an Aliphatic C—H Area to Aromatic C—H Area ratio of at least 25. Since it is believed that the permeation performance of the membrane of the present invention is primarily attributable to the membrane soft segment, this increase in soft segment concentration results in improved separations performance properties for the membrane of the present invention.

The membrane compositions and configurations of the present invention can also be utilized in both unsupported and supported configurations. A non-limiting example of an unsupported membrane configuration includes casting the membrane on a glass plate and subsequently removing it after the chemical cross-linking reaction is completed. Non-limiting examples of supported membrane configurations include casting the membrane onto a support material fabricated from materials such as, but not limited to, polytetrafluoroethylene (e.g., Teflon®), aromatic polyamide fibers (e.g., Nomex® and Kevlar®), porous metals, sintered metals, porous ceramics, polyester, nylon, activated carbon fibers, latex, silicone, permeable (porous) polymers including polyvinylfluoride, polyvinylidenefluoride, polyurethanes, polypropylenes, polyethylenes, polycarbonates, polysulfones, and polyphenylene oxides, metal and polymer foams (open-cell and closed-cell foams), silica, porous glass, mesh screens, and combinations thereof. Preferably, the polymeric membrane support is selected from polytetrafluoroethylene, aromatic polyamide fibers, porous metals, sintered metals, porous ceramics, polyester, nylon, activated carbon fibers, latex, silicone, permeable (porous) polymers including polyvinylfluoride, polyvinylidenefluoride, polyurethanes, polypropylenes, polyethylenes, polycarbonates, polysulfones, and polyphenylene oxides and combinations thereof.

The membrane compositions and configurations of the present invention can be employed in separation processes that employ a membrane in any workable housing configuration such as, but not limited to, flat plate elements, wafer elements, spiral-wound elements, porous monoliths, porous tubes, or hollow fiber elements.

Figure 9:
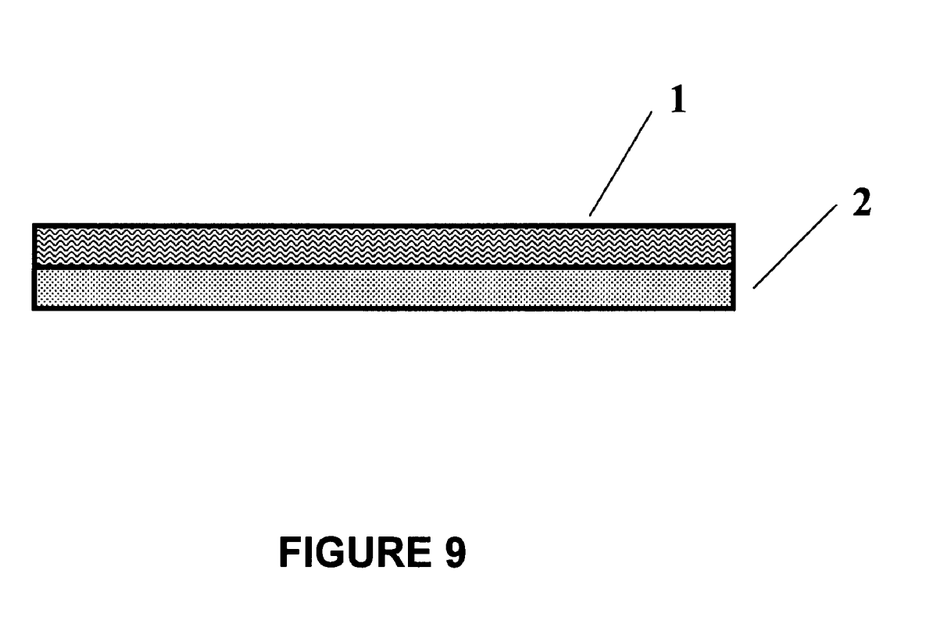
FIG. 9 illustrates one embodiment of a membrane assembly of the present invention wherein the polymeric membrane composition is cast upon a suitable support material.

FIG. 9 is an illustration of a preferred embodiment of a supported membrane assembly of the present invention wherein the membrane copolymer compound (1) is incorporated onto a suitable support material (2). Suitable membrane copolymer compounds and support materials can be selected from those described herein.

The membranes described herein are useful for separating a selected component or species from a liquid feed, a vapor/liquid feed, or a condensing vapor feeds. The resultant membranes of this invention can be utilized in both perstractive and pervaporative separation processes.

In a preferred embodiment, the permeate is removed from the permeate zone by a liquid or vapor sweep stream. The permeate dissolves into the sweep stream and is conducted away by sweep stream flow in order to prevent the accumulation of permeate in the permeate zone.

Membrane separation will preferentially operate at a temperature less than the temperature at which the membrane performance would deteriorate or the membrane would be physically damaged or decomposed. For hydrocarbon separations, the membrane temperature would preferably range from about 32° F. to about 950° F. (0 to 510° C.), and more preferably from about 75° F. to about 500° F. (24 to 260° C.).

In a still another preferred embodiment, the operating pressure range in the retentate zone is from about atmospheric pressure to about 150 psig. The operating pressure ranges in the permeate zone is from about atmospheric pressure to about 1.0 mm Hg absolute.

The membranes of this invention are useful for separating a desired species or component from a feedstream, preferably a hydrocarbon feedstream.

In a preferred embodiment, the membrane compositions and configurations above are utilized for the selective separation of aromatics from a hydrocarbon feedstream containing aromatics and non-aromatics.

In another embodiment, the membrane compositions and configurations above are utilized to selectively separate sulfur and nitrogen heteroatoms from a hydrocarbon stream containing sulfur heteroatoms and nitrogen heteroatoms.

In still another embodiment, the hydrocarbon feedstream is a naphtha with a boiling range of about 80 to about 450° F. (27 to 232° C.), and contains aromatic and non-aromatic hydrocarbons. In a preferred embodiment, the aromatic hydrocarbons are separated from the naphtha feedstream. As used herein, the term naphtha includes thermally cracked naphtha, catalytically cracked naphtha, and straight-run naphtha. Naphtha obtained from fluid catalytic cracking processes ("FCC") are particularly preferred due to their high aromatic content.

Although the present invention has been described in terms of specific embodiments, it is not so limited. Suitable alterations and modifications for operation under specific conditions will be apparent to those skilled in the art. It is therefore intended that the following claims be interpreted as covering all such alterations and modifications as fall within the true spirit and scope of the invention.

EXAMPLES

Example 1

Synthesis of a PEA-DECO Chemically Cross-linked Copolymer Membrane

In the synthesis, 5 g (0.025 moles) of polyethylene adipate (PEA) diol (2000 g/mole) was reacted with 1.09 g (0.005 moles) of pyromellitic dianhydride (PMDA) to make a prepolymer in the end-capping step (165° C. for 6.5 hours). To this solution was added 25 g of dimethylformamide (DMF). The temperature was allowed to decrease to 70° C. A separately prepared solution of 0.67 g (0.0025 moles) of 4,4-methylene bis(2-chloroaniline) (MOCA) dissolved in 5 g DMF was subsequently added. In the DMF solution, one mole of the prepolymer reacts with one mole of MOCA to make a copolymer containing polyamic acid hard segment and PEA soft segment in the chain-extension step. An additional 59.5 g of DMF was then added. Subsequently, 89.5 g of acetone was added to prevent gelling. The resulting solution was then stirred for 1.5 hours at 70° C. The solution was then cooled to room temperature under continual stirring conditions. Diepoxycyclooctane (0.70 g, 0.005 moles) was added to the copolymer-DMF solution at a diepoxide/PEA molar ratio of 2. The result is a 4 wt % polymer solution in 50/50 DMF/acetone.

The final solution was cast onto a porous support of 0.2 micron porous Gore-Tex® Teflon® and the thickness was adjusted by controlling the grams of polymer deposited on the porous Teflon® material to a uniform loading of 0.001576 g/cm$^2$. The membrane casting was first dried at a suitable temperature (e.g., room temperature) to remove most of the solvent (i.e., solvent evaporation), and subsequently low-temperature cured to promote chemical cross-linking at 150° C. (302° F.) for 1.5 hours to promote the reaction of diepoxide with pendent carboxylic acid groups. In the initial drying step, DMF and acetone were evaporated from the membrane in a box purged with nitrogen gas at room temperature for approximately 12 hours. The final curing step converts the polyamide ester hard segment to the polyimide hard segment via the imide ring closure. The final thickness of the membrane polymer coating was approximately 7 microns.

In the synthesis with PEA, PMDA, MOCA and diepoxide at a molar ratio of 1/2/1/2, the chemical cross-linking reaction occurs among pendent carboxylic acid groups adjacent to the ester linkages located between polyimide hard segments and polyester soft segments. The degree of chemical cross-linking can be varied by controlling the concentration of diepoxide incorporated into the multi-block structure.

Example 2

Performance Data of the PEA-DECO Chemically Cross-linked Copolymer Membrane

A 7 micron disc coupon of 5.0 cm (1.97") diameter was cut from the membrane assembly of the PEA-DECO membrane of Example 1. The 7 micron disc was placed on a very fine flat stainless steel screen and sealed in a membrane holder with a teflon o-ring. The membrane holder was maintained at the desired temperature in a thermostated oven. The effective area for each of the membrane assemblies was 17.3 cm$^2$ (2.68 in$^2$).

The membrane coupons were evaluated using a 50% mesitylene/50% decane model feed. The feed was preheated to the desired temperature and flowed over the membrane at 4.54 l/hr (1.2 gal/hr). Inlet pressure was held at approximately 345 kpag (50.0 psig). Membrane temperatures and permeate vacuums were varied during the testing. Permeate was collected under vacuum using traps in series cooled with dry ice and liquid nitrogen respectively.

Table 1 shows the results of using the membrane in separating the aromatic and aliphatic components of the model feed.

TABLE 1

| Membrane Temperature (° C.) | Vacuum Pressure (torr) | Flux (kg/m$^2$-day) | Aromatic Selectivity |
|---|---|---|---|
| 100 | 2.3 | 55.3 | 3.74 |
| 100 | 10.0 | 44.0 | 2.53 |
| 179 | 2.3 | 347.3 | 3.01 |
| 179 | 10.0 | 407.8 | 2.57 |

As can be seen from the data in Table 1, the embodiment of the membrane of the present invention from Example 1 consistently achieved aromatic selectivities of greater than 2.50 and at low vacuum pressures (approximately 2.2 torr), was able to achieve aromatic selectivities of 3.5 and greater. At elevated temperatures (179° C.), the membrane of the present invention was also able to obtain flux rates of over 300 kg/m$^2$-day.

Example 3

Comparison of the PEA-DECO Chemically Cross-linked Copolymer Membrane of the Present Invention to the Prior Art A PEA-DECO chemically cross-linked copolymer membrane of the present invention was synthesized and fabricated as follows:

In the synthesis, 5.0 g (0.0025 moles) of polyethylene adipate (PEA) diol (2000 g/mole) was reacted with 1.09 g (0.005 moles) of pyromellitic dianhydride (PMDA) to make a prepolymer in the end-capping step (165° C. for 7 hours). To this solution was added 25 g of dimethylformamide (DMF). The temperature was allowed to decrease to 70° C. A separately prepared solution of 0.67 g (0.0025 moles) of 4,4-methylene bis(2-chloroaniline) (MOCA) dissolved in 5 g DMF was subsequently added. The solution was stirred at 70° C. for 2.0 hours to prevent gelling. An additional 60 g of DMF and 90.5 g of acetone was added during this time period to prevent gelling. In the DMF/acetone solution, one mole of the prepolymer reacts with one mole of MOCA to make a copolymer containing polyamic acid hard segment and PEA soft segment in the chain-extension step. The solution temperature was allowed to drop to room temperature and 0.70 g (0.005 moles) of Diepoxycyclooctane (DECO) was added to the solution. The solution was stirred at room temperature for 30 minutes. The result was a 4 wt % polymer solution in 50% DMF/50% acetone. An additional 94 g of DMF and 94 g of acetone was added to achieve a 2 wt % polymer solution in 50% DMF/50% acetone.

The 2 wt % polymer solution was centrifuged for 5 minutes. The solution was cast onto a porous support of 0.2 micron porous Gore-Tex® Teflon® and the thickness was adjusted by the use of a knife gap setting of 31 mils. The DMF and acetone was allowed to evaporate at room temperature. The membrane casting was first dried at a suitable temperature (e.g., room temperature) to remove most of the solvent (i.e., solvent evaporation), and subsequently low-temperature cured to promote chemical cross-linking at 180° C. (356° F.) for a minimum cure time of approximately 2.0 hours to promote the reaction of diepoxide with pendent carboxylic acid groups. The final curing step converts the polyamide ester hard segment to the polyimide hard segment via the imide ring closure.

A Diepoxycyclooctane PEI membrane of the prior art was synthesized and fabricated as follows:

In the synthesis, 5.0 g (0.0025 moles) of polyethylene adipate (PEA) diol (2000 g/mole) was reacted with 1.09 g (0.005 moles) of pyromellitic dianhydride (PMDA) to make a prepolymer in the end-capping step (165° C. for 7 hours). To this solution was added 25 g of dimethylformamide (DMF). The temperature was allowed to decrease to 70° C. A separately prepared solution of 0.67 g (0.0025 moles) of 4,4-methylene bis(2-chloroaniline) (MOCA) dissolved in 5 g DMF was subsequently added. The solution was stirred at 70° C. for 2.0 hours to prevent gelling. An additional 60 g of DMF and 90.5 g of acetone was added during this time period to prevent gelling. In the DMF/acetone solution, one mole of the prepolymer reacts with one mole of MOCA to make a copolymer containing polyamic acid hard segment and PEA soft segment in the chain-extension step. The solution temperature was allowed to drop to room temperature and 0.70 g (0.005 moles) of Diepoxycyclooctane (DECO) was added to the solution. The solution was stirred at room temperature for 30 minutes. The result was a 4 wt % polymer solution in 50% DMF/50% acetone. An additional 94 g of DMF and 94 g of acetone was added to achieve a 2 wt % polymer solution in 50% DMF/50% acetone.

The 2 wt % polymer solution was centrifuged for 5 minutes. The solution was cast onto a porous support of 0.2 micron porous Gore-Tex® Teflon® and the thickness was adjusted by the use of a knife gap setting of 31 mils. In the initial drying step, the DMF and acetone were evaporated from the membrane in a box purged with nitrogen gas at room temperature for approximately 6 hours. The membrane was then dried in an oven at 120° C. (248° F.), for about 24 hours. Finally, the membrane was cured at elevated-temperature to promote chemical cross-linking by heating from room temperature to 310° C. (590° F.), maintaining it at this temperature for 144 minutes to promote the reaction of diepoxide with pendent carboxylic acid groups and then cooling it to room temperature. The curing step converts the polyamide ester hard segment to the polyimide hard segment via the imide ring closure.

The Diepoxycyclooctane PEI membrane of the prior art above was made to represent the prior art membranes of U.S. Pat. Nos. 5,550,199 and 5,670,052. Both patents allow diamines to be selected from a group of diamine compounds. For the preparation of these membrane films, 4,4-methylene bis(2-chloroaniline) (MOCA) is used instead of methylene dianiline (MDA). The use of a halogenated diamine compound containing chlorine provides additional analytical capability in analyzing the membrane films. The chlorine atoms contained in the 4,4-methylene bis(2-chloroaniline) (MOCA) can be identified and detected by SIMS and SEM analytical methods. The synthesis methods used were adjusted to reflect the use of 4,4-methylene bis(2-chloroaniline) instead of the methylene dianiline (MDA) used in the examples disclosed in U.S. Pat. Nos. 5,550,199 and 5,670,052. It is believed that the membrane as formulated is an accurate simulation of the membranes of the prior art.

The use of a halogenated diamine compound containing chlorine (such as MOCA) provides additional analytical capability in analyzing the membrane films. The chlorine atoms are a potential tracer compound that is contained in the membrane film that can be analyzed for using a range of analytical methods known to those skilled in the art. This provides a convenient method for distinguishing between different membrane films created by different methods. This additional analytical characterization of membrane films is significantly more complex if compounds like methylene dianiline (MDA) are used in the preparation of the membrane films.

Each of the two as fabricated membranes above were subjected to Infra-red (IR) Reflectance Spectrum analysis. The results of the Reflectance Spectrum testing for the Diepoxycyclooctane PEI membrane of the prior art are shown in FIG. 3 and the results of the Reflectance Spectrum testing for the PEA-DECO chemically cross-linked copolymer membrane of the present invention are shown in FIG. 4. The results of the Reflectance Spectrum data in FIGS. 3 and 4 were then converted to an Absorbance Spectrum using the Kubelka Monk transformation. The Absorbance Spectrum format provides a basis for comparison of the membrane characteristics since the band intensities (absorbance) and integrated areas obtained are proportional to the concentrations of the structural components.

The Absorbance Spectrum shown in FIG. 5 corresponds to the Reflectance Spectrum data in FIG. 3 for the Diepoxycyclooctane PEI membrane of the prior art. The Absorbance Spectrum shown in FIG. 6 corresponds to the Reflectance Spectrum data in FIG. 4 for the PEA-DECO chemically cross-linked copolymer membrane of the present invention.

As can be seen comparing FIGS. 5 and 6, significant differences can be seen in the absorbance values corresponding to the wavenumber values of about 3150 to about 2800 $cm^{-1}$, as well as the wavenumber values of 1875 to 1625 $cm^{-1}$. It should be pointed out that in the Absorbance Spectrum data, that values below about 2.0 are highly linear with respect to concentration and can be used for relative compositional comparison of molecular content within a membrane sample.

FIG. 7 shows an expanded sectional view of the absorbance values corresponding to wavenumber values of about 3150 to 2800 $cm^{-1}$ from FIG. 5 for the Diepoxycyclooctane PEI membrane of the prior art. Similarly, FIG. 8 shows an expanded sectional view of the absorbance values corresponding to wavenumber values of about 3150 to 2800 $cm^{-1}$ from FIG. 6 for the PEA-DECO chemically cross-linked copolymer membrane of the present invention.

In FIGS. 7 and 8, in order to evaluate the relative concentration of the aromatic C—H components associated with the membrane's hard segment and the concentration of the aliphatic C—H components associated with the membrane's soft segment peaked the area defined by the absorbance value curve and a "baseline" must be determined for the particular component. The baseline for the aromatic C—H components is determined by a straight line drawn between the two minima on either side of the aromatic C—H component absorbance peak. In FIGS. 7 and 8, these two minima are at approximately 3150 and 3025 $cm^{-1}$, respectively. The area defined by the integrated area between the absorbance values and the baseline between the two minima defines the Aromatic C—H Area. This Aromatic C—H Area is proportional to the hard segment content of the final polymer membrane.

In a similar manner, the baseline for the aliphatic C—H components is determined by a straight line drawn between the two minima on either side of the aliphatic C—H component absorbance peak. In FIGS. 7 and 8, these two minima are at approximately 3025 and 2800 $cm^{-1}$, respectively. The area defined by the integrated area between the absorbance values and the baseline between the two minima defines the Aliphatic C—H Area. This Aliphatic C—H Area is proportional to the soft segment content of the final polymer membrane. The determination of the value of the Aliphatic C—H Area and Aromatic C—H Area for membrane sample as utilized herein is defined by this procedure.

Comparing these areas for the Diepoxycyclooctane PEI membrane of the prior art (FIG. 7) and the PEA-DECO chemically cross-linked copolymer membrane of the present invention (FIG. 8), it can be seen that the PEA-DECO chemically cross-linked copolymer membrane of the present invention in FIG. 8 shows a significant peak in the absorbance values corresponding to wavenumber values of about 3025 to about 2800 $cm^{-1}$ as compared with the same values in the prior art membrane shown in FIG. 7. This shows that the membrane of the present invention possess a significantly higher ratio of the aliphatic C—H soft segment as compared to the aromatic C—H hard segment.

While the absolute areas nor the absolute absorbance values between FIG. 7 and FIG. 8 should not be compared directly, the Aliphatic C—H Area/Aromatic C—H Area ratio (also referred to herein as the "Aliphatic C—H Area to Aromatic C—H Area ratio") for a given membrane is an accurate measurement of the relative concentrations of the Aromatic C—H components and the Aliphatic C—H components of the membrane. Therefore, the ratio of these areas is a suitable measurement for direct comparison of two different polymer membrane specimens. As can be seen comparing FIGS. 7 and 8, the Ratio of Aliphatic C—H Area/Aromatic C—H Area is about 1.39 for the Diepoxycyclooctane PEI membrane of the prior art. In contrast, the Ratio of Aliphatic C—H Area/Aromatic C—H Area is about 25.00 for the PEA-DECO chemically cross-linked copolymer membrane of the present invention.

As illustrated by this example, the membranes of the present invention posses significantly improved structural properties over the prior art.

What is claimed is:

1. A process for forming an appropriately selective membrane element within a membrane assembly and for using that membrane assembly for selectively separating a desired component from a hydrocarbon feedstream, the process comprising:
   a) forming a first membrane element comprised of a dianhydride, a halogenated diamine, an epoxy cross-linking agent, and a $C_1$ to $C_{18}$ polyalkyladipate difunctional dihydroxy polymer, and wherein the first membrane element has a retentate side and a permeate side and is comprised of a hard segment and soft segment, wherein the soft segment has a glass transition temperature, $T_g$, less than 77° F. (25° C.);
   b) analyzing the first membrane element by infra-red spectroscopy to determine an Absorbance Infra-red Spectrum, so as to determine an Aliphatic C—H Area, defined by an absorbance peak and a baseline at wavenumbers approximately between 3150 and 3025 $cm^{-1}$, and an Aromatic C—H Area, defined by an absorbance peak and a baseline at wavenumbers approximately between 3025 and 2800 $cm^{-1}$;
   c) for membrane elements having a ratio of the Aliphatic C—H Area to the Aromatic C—H Area of at least 10, forming a polymeric membrane assembly comprised of at least the first membrane element and at least a first support material;
   (d) contacting the retentate side of the polymeric membrane assembly with the hydrocarbon feedstream; and
   (e) retrieving a permeate stream from the permeate side of the polymeric membrane assembly;
   wherein the concentration by wt % of the desired component in the permeate stream is higher than the concentration by wt % of the desired component in the hydrocarbon feedstream.

2. The process of claim 1, wherein the desired component is an aromatic compound.

3. The process of claim 1, wherein the desired component is a sulfur heteroatom.

4. The process of claim 1, wherein the desired component is a nitrogen heteroatom.

5. The process of claim 1, wherein the first support material is selected from polytetrafluoroethylene, aromatic polyamide fiber, porous metal, sintered metal, porous ceramic, polyester, nylon, activated carbon fiber, latex, silicone, polyvinylfluoride, polyvinylidenefluoride, polyurethane, polypropylene, polyethylene, polycarbonate, polysulfone, polyphenylene oxide, metal foam, polymer foam, silica, porous glass, mesh screen, and combinations thereof.

6. The process of claim 5, wherein the first membrane element and the first support material are incorporated into a support: configuration selected from flat plate elements, wafer elements, spiral-wound elements, porous monoliths, porous tubes, and hollow fiber elements.

7. The process of claim 6, wherein the first membrane element is comprised of a cross-linking agent selected from diepoxycyclooctane, diepoxyoctane, 1,3-butadiene diepoxide, glycerol diglycidyl ether, bisphenol A diglycidyl ether, 1,4-butanediol diglycidyl ether, 1,4-cyclohexanedimethanol diglycidyl ether, bisphenol F diglycidyl ether, neopentyl glycol diglycidyl ether, poly(propylene glycol) diglycidyl ether, and mixtures thereof.

8. The process of claim 7, wherein the hydrocarbon feedstream is comprised of a naphtha with a boiling range of about 80 to about 450° F. (27 to 232° C.).

9. The process of claim 8, wherein the wherein the desired component is an aromatic compound.

10. The process of claim 7, wherein the glass transition temperature, Tg, of the soft segment of the first membrane element is less than 32° F. (0° C.).

11. The process of claim 9, wherein the glass transition temperature, Tg, of the soft segment of the first membrane element is less than 32° F. (0° C.), and the Aliphatic C—H Area to Aromatic C—H Area ratio is at least 20.

12. The process of claim 11, wherein the glass transition temperature, Tg, of the soft segment of the membrane element is less than −13° F. (−25° C.) and the Tg of the hard segment of the membrane element is greater than 248° F. (120° C.).

13. The process of claim 1, wherein the halogenated diamine comprises 4,4-methylene-bis(2-chloroaniline) (MOCA).

14. The process of claim 1, wherein the C1 to C18 polyalkyladipate difunctional dihydroxy polymer is a polyethylene adipate (PEA), the dianhydride is pyromellitic dianhydride (PMDA), the halogenated diamine is 4,4-methylene-bis (2-chloroaniline) (MOCA), and the epoxy cross-linking agent is diepoxycyclooctane (DECO).

* * * * *